(12) United States Patent
Orjales Venero et al.

(10) Patent No.: US 6,413,966 B1
(45) Date of Patent: Jul. 2, 2002

(54) ARYLPIPERAZINYLALKYL-3(2-H)-PYRIDAZINONES

(75) Inventors: Aurelio Orjales Venero, Neguri; Neftali Garcia-Dominguez, Getxo, both of (ES)

(73) Assignee: FAES, Fabrica Espanola de Productos Quimicos y Farmaceuticos, S.A.

( * ) Notice: Subject to any disclaimer, the term of this patent is extended or adjusted under 35 U.S.C. 154(b) by 0 days.

(21) Appl. No.: 09/586,001

(22) Filed: Jun. 2, 2000

(30) Foreign Application Priority Data

Jun. 4, 1999 (ES) ................................ 9901239

(51) Int. Cl.[7] ..................... A61K 31/501; C07D 403/06
(52) U.S. Cl. ................... 514/252.02; 544/238
(58) Field of Search ....................... 544/238; 514/252.02

(56) References Cited

PUBLICATIONS

Corsano et al., *Eur. J. Med. Chem. 32*, p. 339–342, 1997.*
Umio et al, *Chemical Abstracts*, vol. 71, No. 91521 (Abstract for JP 69 18307 Aug. 11, 1969).*

* cited by examiner

*Primary Examiner*—Emily Bernhardt
(74) *Attorney, Agent, or Firm*—Lackenbach Siegel LLP

(57) ABSTRACT

A description is given of new arylpiperazinylalkyl-3(2H)-pyridazinones of general formula (I) and their preparation and their addition salts with pharmaceutically acceptable acids,

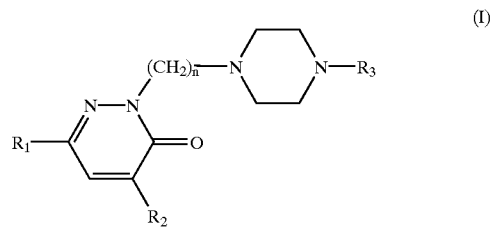

in which $R_1$ is a methyl or phenyl radical, $R_2$ is a hydrogen atom or a methyl radical, n takes values between 2 and 4, and $R_3$ is a naphthyl radical or a phenyl radical, which are substituted by a radical such as methoxyl, trifluoromethyl and chlorine.

The compounds have affinity for serotonin $5HT_{1A}$ and $5HT_2$ receptors and for dopamine $D_2$ receptors, and can be useful as antipsychotics.

2 Claims, No Drawings

ARYLPIPERAZINYLALKYL-3(2-H)-PYRIDAZINONES

The present invention relates to the preparation of new arylpiperazinylalkyl-3(2H)-pyridazinones and their addition salts. The new compounds present serotonergic and central dopaminergic activity, which makes them useful as antipsychotics.

The most widely accepted theory explaining the biochemical bases of schizophrenia holds that the dopaminergic activity in the mesolimb system of the brain is increased and, accordingly, the pharmacological power of classic antipsychotics is correlated with their affinity for $D_2$ receptors (Science 1976, 1982, 481–483). It has further been proposed (J. Pharm. Exp. Ther., 1989, 251, 238–246) that the high affinity for $5HT_{1A}$ receptors is responsible for the beneficial effects of the pharmacological profile of atypical antipsychotics. It has moreover been found (J. Neurol. Transm., 1983, 57, 255) that $5HT_{1A}$ agonists are capable of inverting haloperidol-induced catalepsy. Consequently, many compounds composite affinity for $5HT_{1A}$, $5HT_2$ and $D_2$ receptors, claimed as atypical antipsychotics (Advances in Med. Chem., 3, 1995, 1–55).

Antipsychotic compounds heretofore described belong in several chemical families, which are only sometimes interrelated, with structures differing essentially from the 3(2H)-pyridazinones subject of this invention.

European Patent EP 0329168 describes a number of 1,4-disubstituted piperazines with psychotropic activity, in which the 1-substituent is a bicyclic heterocycle which incorporates an amide or imide function and the 4-substituent is another heterocycle, which differ from those described herein, wherein the alkyl-3(2H)-pyridazinone fragment is the 1-substituent and a non-heterocyclic cyclic system is the 4-substituent.

J. Med. Chem. 1994, 37, 1060–1062 describes a number of phenylpiperazines having a high affinity for $D_2$, $D_3$, $5HT_{1A}$ and $\alpha_{1A}$ receptors, providing them with interesting antipsychotic properties, moreover presenting a low potential for causing extrapyramidal effects. These phenylpiperazines are clearly distinguished from those described herein in the fragment bound to piperazine.

Patent WO 93/16073 claims arylpiperidines and arylpiperazines with $D_2$ and $5HT_2$ receptor antagonist properties, useful in the treatment of psychosis, though said compounds are characterised by having a heterobycyclic system at the 4-position of piperazine or piperidine, which clearly distinguishes them from the compounds described in the present invention.

Patent ES 9700812 (C.A.: 129:343506) finally describes a number of naphthylpiperazines having a high affinity for $5HT_{1A}$, $5HT_2$ and $D_2$ receptors, potentially useful as antipsychotics, containing a phthalazinone rest in their structure which characterises them as to their chemical structure and distinguishes them from those described herein.

In existing reference works a number of 1-aminoalkyl-3(2H)-pyridazinones carrying a [1,4]-benzodioxanylmethylamine or phenoxyalkylamine group can also be found, as contained in Eur. J. Med. Chem. 1992, 27, 107–114, although they are described as blocking $\alpha$-adrenoreceptors and having antihypertensive activity, distinguishing them pharmacologically from those described herein, since those claimed in the present invention have affinity for dopamine and serotonin receptors, with respect to the central nervous system. Furthermore, these pyridazinones are structurally different from those described in the present invention, due to the presence of the benzodioxanylmethylamine or phenoxyalkylamine fragment, whereas those described herein carry a diversely substituted arylpiperazinoalkyl fragment.

The compounds described in the present invention are essentially different from all those referred to in the above-mentioned publications. due to the presence of the 3(2H)-pyridazinone grouping, which pharmacologically characterises them and provides them with a great affinity for serotonin $5HT_{1A}$ and $5HT_2$ receptors as well as dopamine $D_2$ receptors, and they are therefore useful as atypical antipsychotics.

DESCRIPTION

The present invention relates to the preparation of new arylpiperazinylalkyl-3(2H)-pyridazinones of formula (I) and their addition salts with pharmaceutically acceptable acids,

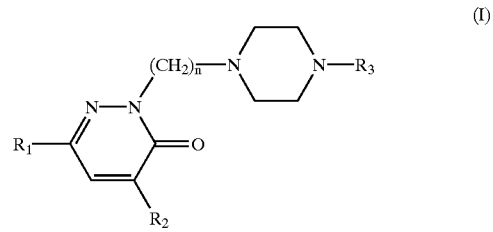

(I)

in which $R_1$ is a methyl or phenyl group,
$R_2$ is a hydrogen atom or a methyl group
n takes values between 2 and 4
and $R_3$ is a naphthyl radical or a phenyl radical which may be substituted by a radical such as methoxyl, chlorine, trifluoromethyl.

The preparation of compounds of formula (I) can be carried out along various synthetic routes, using conventional methods:

Condensation of a compound of formula (II)

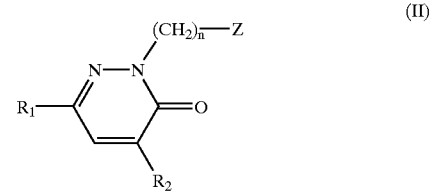

(II)

in which $R_1$, $R_2$ and n have the meaning specified for formula (I) and Z is chlorine or bromine, with a piperazine of formula (III)

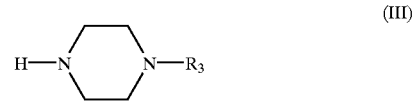

(III)

The reaction is carried out in an inert solvent, in the presence of a base, and at a temperature ranging between 20° C. and the boiling point of the reaction mixture.

The solvent used is dichloromethane, chloroform, acetonitrile, dimethylformamide or tetrahydrofurane.

The base used can be an alkaline carbonate or bicarbonate, such as $K_2CO_3$, $KHCO_3$, $Na_2CO_3$, $NaHCO_3$ or a tertiary amine such as pyridine or triethylamine.

The reaction rate may be increased by adding catalytic amounts of an alkaline iodide, such as KI to the reaction mixture.

The piperazines of formula (III) are commercially available, when $R_3$ is phenyl or phenyl-substituted, and are prepared by reacting bis (2-chloroethyl)amine with the conveniently substituted naphthylamine., when $R_3$ is naphthyl or naphthyl-substituted.

The compounds of general formula (II) used at the previous condensation stage are prepared by reactin compound of general formula (IV)

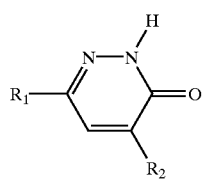

(IV)

in which $R_1$ and $R_2$ have been previously defined, with an alkyl dihalide in the presence of a strong base, such as NaH in an aprotic solvent such as dimethylformamide or tetrahydrofurane, or solid potassium hydroxide in dimethylformamide, at a temperature ranging between room temperature and 100° C.

The compounds of general formula (IV) are commercially available or are prepared by reacting suitable 2-benzoylpropionic acids with hydrazine hydrate.

Alternately, compounds of general formula (II) can be prepared by means of a substitution of the hydroxyl group with chlorine or bromine in compounds of formula (V), obtained in accordance with the method described in Chimie Therapeutique, 1967, 2, 250–253.

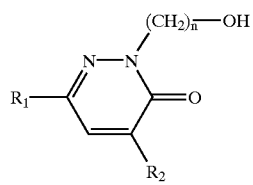

(V)

The substitution reaction can be carried out by treatment of (V) with hydrogen chloride, hydrogen bromide, with organic or inorganic acid halides, such as oxalyl chloride or thionyl chloride, in an inert solvent such as chloroform, dichloromethane, or toluene, or using the acid chloride as a solvent, at a temperature ranging between 0° C. and the boiling point of the reaction mixture.

Pharmacological Studies

As noted hereinbefore, the new compounds of general formula (I), in accordance with the present invention, show SNC activity, more specifically at the $5HT_{1A}$, $5HT_2$ and $D_2$ receptor levels.

Binding studies of the compounds described in the present invention have been carried out to ascertain the affinity of the compounds for $5HT_{1A}$, $5HT_2$ and $D_2$ receptors.

$5HT_{1A}$ Receptor

Cerebral cortex taken from both male and female Wistar rats was homogenised in saccharose buffer 0.32 M (1:10 g/mL) and centrifuged at 900 g (10 min, 4° C.). The supernatant was collected and centrifuged at 48000 g (25 min, 4° C.). The sediment thus obtained was re-suspended in cold TRIS buffer 50 mM (pH 7.5, 1:10, g/mL), homogenised, incubated at 37° C. for 15 min and centrifuged again at 48000 g (25 min, 4° C.). The final sediment was re-suspended in cold SNAYDER buffer (1:4, g/mL), homogenised and kept at −70° C. in 5 mL containers.

For the displacement trial, 100 μL of radioligand (2 nM, final conc.), 100 μL of the different tested concentrations of the displacing product and 750 μL of a suspension of membranes 1:32 in SNAYDER with pargilin were used. The volume was topped up to 1 mL with 50 μL of SNAYDER. Serotonin (5HT) 10 μM was used to define the non-specific binding.

$5HT_2A$ Receptor

Prefrontal cortex taken from both male and female Wistar rats was homogenised in saccharose buffer 0.25 M (1:10 g/mL) and centrifuged at 1080 g (10 min, 4° C.). The supernatant was set aside and the pellet re-suspended in the same buffer (1:5, g/mL) and centrifuged again under the same conditions. The mixture of both supernatants was topped up to 1:40 (g/mL) with TRIS buffer 50 mM (pH 7.7) and centrifuged at 35000 g (10 min, 4° C.). The sediment thus obtained was re-suspended in cold TRIS buffer (1:40, g/mL) and centrifuged again at 35000 g (10 min, 4° C.). The final sediment was re-suspended in cold TRIS buffer (1:10, g/mL), homogenised and kept at −70° C. in 5 mL containers.

For the displacement trial, 100 μL of radioligand (0.5–1 nM, final concentration), 100 μL of the different tested concentrations of the displacing product and 750, μL of a suspension of membranes 1:50 (0.54 mg/mL, 15 mg fresh tissue) in TRIS were used. The volume was topped up to 1 mL with 50 μL of TRIS/10% ethanol. Metisergide 1 μM was used to define the non-specific binding. The displacer, radioligand and Metisergide dilutions were all made with TRIS buffer with 10% ethanol (v/v).

$D_2$ Receptor

Corpus striatum taken from both male and female Wistar rats was homogenised in TRIS buffer 50 mM (pH 7.7, 1:50 g/mL) and centrifuged at 47800 g (10 min, 4° C.). The supernatant was eliminated and the pellet re-suspended in the same buffer (1:50, g/mL), incubated at 37° C. for 10 min and centrifuged again under the same conditions.

The final sediment thus obtained was re-suspended in cold TRIS buffer 50 mM (pH 7.4, 1:10, g/mL) containing NaCl 120 mM+KCl 5 mM+$CaCl_2$ 2 mM+$MgCl_2$ 1 mM+ascorbic acid 0.01% g/mL, and kept at −70° C. in 2.5 mL aliquots. Membrane dilutions (1:100–1:300) were subsequently carried out and the amount of proteins was assessed by the Lowry method.

For the displacement test, 100 μL of radioligand (1–2 nM, final conc.), 100 μL of the different tested concentrations of the displacing product and 750 μL of a suspension of membranes 1:150 (0.39–0.43 protein mg/mL) in the previous (saline) TRIS+10 μM of pargilin were used. The volume was topped up to 1 mL with 50 μL of the previous TRIS. Butachlamol 1μM was used to define the non-specific binding, which was added (100μL) to the BLANK series. The displacer, radioligand and Butachlamol dilutions were all made with TRIS (saline) buffer+pargilin. The samples were incubated for 60 min at 25° C.

The products described in the present invention have all shown a high (nanomolar range) affinity for the three tested receptors, which renders them potentially useful as antipsychotics.

The following examples provide further details of the invention, which is not howsoever limited to such examples.

EXAMPLE 1

2-(4-Bromobutyl)-6-methyl-3(2H)-pyridazinone

Small portions (0.83 g, 20 mmol) of a dispersion of 60% NaH in mineral oil were added over a solution of 6-methyl-3(2H)-pyridazinone (1.3 g, 12 mmol) in dimethylformamide (30 mL) cooled to 0° C. The reaction mixture was left to reach room temperature and kept stirred for an hour. It was then cooled with an ice bath and 1,4-dibromobutane (4.8 mL, 40 mmol) was then added at a time and the reaction mixture was stirred, at room temperature, for 16 hours. The reaction mixture was poured over crushed ice, extracted with ethyl ether (twice), and the organic extracts were dried over anhydrous $Na_2SO_4$ and concentrated to dryness. The excess dibromobutane was eliminated by distillation and the obtained residue was purified by flash chromatography ($CH_2Cl_2$), yielding an oil (2.3 g, yield: 78%) identified on the basis of its spectroscopic data as the title product.

EXAMPLE 2

2-[4-(4-Naphthylpiperazine-1-yl)-butyl]-6-methyl-3(2H)-pyridazinone

A mixture of 2-(4-bromobutyl)-6-methyl-3(2H)-pyridazinone (2.3 g, 9.5 mmol), 1-naphthylpiperazine (1.7 g, 8 mmol), $K_2CO_3$ (1.12 g, 8 mmol), and KI (10 mg) in acetonitrile (50 mL) was stirred at room temperature for 48 hours. Thereafter, the solvent was eliminated at reduced pressure and the residue distributed between dichloromethane and water; the aqueous phase was extracted with dichloromethane (twice). The organic extracts were collected, dried over anhydrous $Na_2SO_4$ and concentrated to dryness. The obtained residue was purified by flash chromatography ($CH_2Cl_2$/MeOH 96:4), yielding 2-[4-(4-naphthylpiperazine-1-yl)-butyl]-6-methyl-3(2H)-pyridazinone (2.4 g). The product was dissolved in ethanol and by adding hydrochloric acid concentrated up to a pH=1 yielded a white solid, which was re-crystallised in methanol, yielding the hydrochloride of the title compound, presenting a M.P. higher than 260° C.

EXAMPLE 3

2-(2-Hydroxyethyl)-6-phenyl-3(2H)-pyridazinone

A mixture of 6-phenyl-3(2H)-pyridazinone potassium salt (10 mmol) (prepared from 6-phenyl-3(2H)-pyridazinone (1.72 g; 10 mmol) and KOH in methanol (0.56 g; 10 mmol), 2-bromoethanol (12 mmol), TBAB (1.19 g; 4 mmol) and atomised KOH (11 mmol) in toluene (60 mL) was stirred at room temperature for 6 hours. The reaction mixture was filtered, the filtrate was washed successively with 5% NaOH solution, 10% HCl solution and lastly water. The organic extracts were dried over anhydrous $Na_2SO_4$ and concentrated to dryness, and the obtained residue was purified by flash chromatography ($CH_{22}Cl_2MeOH$ 98:2), yielding the title product (1.9 g).

EXAMPLE 4

2-(2-Chloroethyl)-6-phenyl-3(2H)-pyridazinone

Thionyl chloride (15 mmol) was added to a solution of 2-[2-(hydroxyethyl)]-6-phenyl-3(2H)-pyridazinone (2.2 g; 10 mmol) in chloroform (50 mL) and the mixture was kept stirred at room temperature overnight. The solvent was eliminated at reduced pressure, and the obtained residue was treated with hexane, concentrated to dryness (twice) and purified by flash chromatography ($CH_2Cl_2$), yielding 2-(2-chloroethyl)-6-phenyl-3(2H)-pyridazinone as an oil (1.9 g, yield: 75.6%).

EXAMPLE 5

2-[2-(4-Naphthylpiperazine-1-yl)-ethyl]-6-phenyl-3(2H)-pyridazinone

A mixture of 2-(2-chloroethyl)-6-phenyl-3(2H)-pyridazinone (1.9 g, 7.5 mmol), 1-naphthylpiperazine (1.7 g, 8 mmol), $K_2CO_3$ (1.12 g, 8 mmol) and KI (10 mg) in acetonitrile (50 mL) was refluxed for 7 hours. When heating, was over, the solvent was eliminated at reduced pressure and distributed between dichloromethane and water; the aqueous phase was extracted with dichloromethane (twice). The organic extracts were collected, dried over anhydrous $Na_2SO_4$ and concentrated to dryness. The obtained residue was purified by flash chromatography ($CH_2Cl_2$/MeOH 97:3) yielding 2-[2-(4-naphthylpiperazine-1-yl)-ethyl]-6-phenyl-3(2H)-pyridazinone (2.1 g). The product was dissolved in ethanol and by adding hydrochloric acid concentrated up to pH=1 yielded a white solid, which was re-crystallised in methanol, yielding the hydrochloride of the title compound, presenting a M.P. higher than 260° C.

The compounds listed in table 1 were analogously prepared.

TABLE 1

| Compound | $R_1$ | $R_2$ | $R_3$ | n | M.P. ° C. (HCl) |
|---|---|---|---|---|---|
| 1 | Phenyl | H | 1-Naphthyl | 4 | 202–04 |
| 2 | Phenyl | H | 1-Naphthyl | 3 | 239–24 |
| 3 | Methyl | H | 1-Naphthyl | 4 | 236–38 |
| 4 | Methyl | H | 1-Naphthyl | 3 | >240 |
| 5 | Methyl | H | 1-Naphthyl | 2 | 219–221 |
| 6 | Methyl | H | 6-methoxy-1-naphthyl | 4 | 190 (dec.) |
| 7 | Phenyl | H | o-Methoxyphenyl | 4 | 213–15 |
| 8 | Phenyl | H | m-Chlorophenyl | 4 | 186–88 |
| 9 | Phenyl | H | m-Chlorophenyl | 3 | 202–204 |
| 10 | Phenyl | H | m-Chlorophenyl | 2 | >250 |
| 11 | Phenyl | H | m-Trifluoromethylphenyl | 4 | 181–83 |
| 12 | Phenyl | H | m-Trifluoromethylphenyl | 3 | 206–209 |
| 13 | Phenyl | H | m-Trifluoromethylphenyl | 2 | 225 (dec.) |
| 14 | Methyl | H | o-Methoxyphenyl | 4 | 205–207 |
| 15 | Methyl | H | o-Methoxyphenyl | 2 | 220 (dec.) |
| 16 | Methyl | H | m-Chlorophenyl | 4 | 170–72 |
| 17 | Methyl | H | m-Chlorophenyl | 3 | 187–89 |
| 18 | Methyl | H | m-Trifluoromethylphenyl | 4 | 190–92 |
| 19 | Methyl | H | m-Trifluoromethylphenyl | 3 | 195–199 |
| 20 | Methyl | H | m-Trifluoromethylphenyl | 2 | >250 |
| 21 | Phenyl | Methyl | o-Methoxyphenyl | 4 | 202–5 |
| 22 | Phenyl | Methyl | m-Chlorophenyl | 4 | 207–10 |
| 23 | Phenyl | Methyl | m-Chlorophenyl | 3 | 213–13 |
| 24 | Phenyl | Methyl | m-Trifluoromethylphenyl | 4 | 177–80 |

What is claimed:

1. A compound isolated as a base or an addition salt with a pharmaceutically acceptable acid, selected from 6-phenyl-2-[4-(4-naphthylpiperazine-1-yl)butyl]-3(2H) pyridazinone 6-phenyl-2-[3-(4-naphthylpiperazine-1-yl)propyl]-3(2H) pyridazinone 6-methyl-2-[4-(4-naphthylpiperazine-1-yl)butyl]-3(2H)pyridazinone 6-methyl-2-[3-(4-naphthylpiperazine-1-yl)propyl]-3(2H)pyridazinone 6-methyl-2-[2-(4-naphthylpiperazine-1-yl)ethyl]-3(2H)pyridazinone 6-methyl-2-[4-[4-6-methoxy-1-naphthyl)piperazine-1-yl)butyl]-3(2H)pyridazinone 6-phenyl-2-[4-[4-(3-chlorophenyl)piperazine-1-yl)butyl]-3(2H)pyridazinone 6-phenyl-2-[3-[4-(3-chlorophenyl)piperazine-1-yl)propyl]-3(2H)pyridazinone 6-phenyl-2-[2-[4-(3-chlorophenyl)piperazine-1-yl)ethyl]-3(2H)pyridazinone 6-phenyl-2-[4-[4-(3-trifluoromethyl)phenylpiperazine-1-yl)butyl]-3(2H)pyridazinone 6-phenyl-2-[3-[4-(3-trifluoromethyl)phenylpiperazine-1-yl)propyl]-3(2H)pyridazinone 6-phenyl-2-[2-[4-(3-trifluoromethyl)phenylpiperazine-1-yl)ethyl]-3(2H)pyridazinone 6-methyl-2-[4-[4-(2-methoxyphenyl)piperazine-1-yl)butyl]-3(2H)pyridazinone 6-methyl-2-[2-[4-(2-methoxyphenyl)piperazine-1-yl)ethyl]-3(2H)pyridazinone 6-methyl-2-[4-[4-(3-chlorophenyl)piperazine-1-yl)butyl]-3(2H)pyridazinone 6-methyl-2-[3-[4-(3-chlorophenyl)piperazine-1-yl)propyl]-3(2H)pyridazinone 6-methyl-2-[4-[4-(3-trifluoromethylphenylpiperazine-1-yl)butyl]-3(2H)pyridazinone 6-methyl-2-[3-[4-(3-trifluoromethylphenylpiperazine-1-yl)butyl]-3(2H)pyridazinone.

2. A composition for treating pyschosis containing a therapeutically effective quantity of the compound of claim 1.

\* \* \* \* \*